(12) United States Patent
Berard (10) Patent No.: US 10,682,660 B1
(45) Date of Patent: Jun. 16, 2020

(54) SCENT SAMPLER

(71) Applicant: Scentisphere LLC, Carmel, NY (US)

(72) Inventor: James Berard, Pleasantville, NY (US)

(73) Assignee: Scentisphere LLC, Carmel, NY (US)

( * ) Notice: Subject to any disclaimer, the term of this patent is extended or adjusted under 35 U.S.C. 154(b) by 314 days.

(21) Appl. No.: 15/450,946

(22) Filed: Mar. 6, 2017

Related U.S. Application Data (60) Provisional application No. 62/304,681, filed on Mar. 7, 2016.

(51) Int. Cl.
  *B05B 11/04* (2006.01)
  *A61L 9/12* (2006.01)
  *A45D 34/02* (2006.01)
  *A45D 40/00* (2006.01)

(52) U.S. Cl.
  CPC ............ *B05B 11/048* (2013.01); *A45D 34/02* (2013.01); *A45D 40/0087* (2013.01); *A61L 9/12* (2013.01)

(58) Field of Classification Search
  CPC ... B05B 11/048; A45D 34/02; A45D 40/0087; A61L 9/12
  See application file for complete search history.

(56) References Cited

U.S. PATENT DOCUMENTS

| | | | | |
|---|---|---|---|---|
| 1,239,584 A | * | 9/1917 | Frank | ........................ A61L 9/12 239/36 |
| 7,798,422 B2 | * | 9/2010 | Trevino | ................... A61L 9/127 239/145 |

* cited by examiner

*Primary Examiner* — Christopher S Kim
(74) *Attorney, Agent, or Firm* — Mandelbaum Silfin Economou LLP (57) ABSTRACT

A scent sampler has a compressible and expandable housing in which there is a chamber containing a resilient, compressible, absorbent, elastic reservoir for absorbing a scented liquid. The housing is formed from two bin-like members made of a form sustainable material, one inverted relative to and telescopically captured within the other for relative reciprocation. Squeezing of the housing urges the housing members to telescope toward one another thereby reducing the volume and increasing the pressure in the chamber for forcing vapor in the chamber into the ambient environment through an opening in the housing.

10 Claims, 11 Drawing Sheets

SCENT SAMPLER

BACKGROUND OF THE INVENTION

Until the present invention, there has been no entirely satisfactory way of enabling consumers at a point of sale to sample the scent of a fragrance product such as a deodorant, room air freshener, car air freshener, fabric softener, candle, and the like. Atomizers commonly used to spray perfumes emit a liquid that can be harmful to the eyes, dangerous to children, or cause damage to in-store fixtures and nearby merchandise.

It is known to place within a container made of a flexible resilient plastic material, a porous item into which a fragrance material has been absorbed as disclosed in U.S. Pat. No. 6,736,335 to Cuthbert. Fragrance evaporates into the air within the container. When the container is squeezed, the resilient walls are urged inwardly to pump an air fragrance mixture within the container through an opening to the ambient environment. In such a device, the porous material serves to store the fragrance while the resilient walls of the container provide the necessary resilience for restoring the container to a relaxed position whereat the container is filled with air from the ambient atmosphere. A disadvantage of such a construction is that, over time, flexing and unflexing of the container walls can leak and ultimately lead to rupture of the plastic from which the container is made. Also, the porous item tends to dry out quickly thereby limiting the useful life of the device as a scent dispenser.

Another approach found in U.S. Pat. No. 8,777,127 to Bernstein is to employ a container made of paper or flexible cardboard into which a resilient wafer has been placed. The paper or cardboard container is sealed along its edges and the resilient wafer provides the spring force necessary to restore the volume of the container after it is reduced by squeezing the container walls together thereby compressing the wafer.

The use of cardboard in a scent sampler at a point of purchase display can convey an impression of shoddiness or inferiority, especially after use over a prolonged period of time, as such constructions are subject to damage and wear. Moreover, because the space with a cardboard container sealed at the edges is narrower at the edges than near in the center, the scent carrying wafer must be affixed to an inside surface to prevent its becoming wedged in near the edges which can reduce its effectiveness in restoring the volume of the container when released.

The present invention overcomes the aforementioned problems of the prior art in providing a construction formed from substantially rigid and, hence, strong materials. Such a constructing is more impressive to consumers and conveys the feeling of a higher quality product than is the case with a cardboard construction.

SUMMARY OF THE INVENTION

In accordance with the invention, a reservoir in the form of a block of a resilient compressible spongy absorbent hydrophilic material, e.g., foam material, is inserted in a chamber of a variable size housing formed by two bin shaped members which are mounted together so that one of the housing members can telescope within the other for compressing the resilient reservoir when the members are squeezed together and urging the housing members apart when the resilient reservoir restores itself to its expanded uncompressed state upon release of the squeezing force.

A fragrance liquid is absorbed into the resilient reservoir before insertion of the reservoir into the chamber to be formed by assembly of the housing members. The liquid evaporates from the reservoir causing a vapor of the fragrance liquid to mix with the air within the housing.

When the user applies pressure to the housing, e.g., by squeezing, the housing members telescope toward one another thereby reducing the volume and increasing the pressure in the chamber and, thereby, forcing vapor in the chamber through the opening for scenting the surrounding air whereby the scent of the fragrance liquid can be sampled, i.e., sniffed and evaluated, by the user. Contemporaneously, the reservoir is compressed.

When pressure on the housing members is relieved, the resiliency of the compressible spongy absorbent material urges the housing members apart to a position of maximum separation whereat an outward projecting lip circumscribing an edge of an inner one of the housing members engages an inward projecting shoulder circumscribing an edge of an outer one of the housing members for preventing complete separation of the housing members. In this manner, the inner housing member is able to telescope within the outer housing member while the two housing members are captured together.

Thus the scent sampler of the invention has a compressible and expandable housing with top and bottom bin-like members, one inverted relative to and telescopically mounted within the other for relative reciprocation along an axis, between maximum and minimum separation of the top and bottom members, the top member having a ceiling and the bottom member having a floor substantially transverse to the axis and a circumferential wall extending orthogonally inwardly from the major wall in a direction parallel to the axis.

Inside the housing is a chamber of variable volume enclosed by the ceiling, the floor, the circumferential wall of the top member and the circumferential wall of the bottom member, The housing has an aperture through which air can travel between the chamber and the ambient environment. An outer surface of the circumferential wall of the top member is in frictional sliding engagement with an inner surface the circumferential wall of the bottom member.

A resilient, compressible, absorbent, elastic reservoir within the chamber has absorbed within it a scented liquid. The reservoir is preferably formed from a spongy, hydrophilic material.

The reservoir has a dimension greater than the minimum separation so that during squeezing of the top and bottom members toward one another, the reservoir is compressed and releases into the chamber a vapor of the scented liquid which forms a mixture with the air in the chamber. At that time a portion of the mixture is released into the ambient environment through the aperture. Upon cessation of the squeezing, the reservoir urges the top and bottom members apart toward maximum separation as the reservoir returns to an uncompressed state drawing ambient air from the ambient environment into the chamber.

The bottom member has, along an edge of its circumferential wall distal from its floor, a shoulder extending inwardly in a direction generally parallel to the floor. The top member has, along an edge of its circumferential wall distal from the ceiling, a lip extending outwardly in a direction generally parallel to the ceiling in interfering relationship to the shoulder for capturing the top member within the bottom member and preventing complete separation of the top member and the bottom member.

At least one of the top member and the bottom member is made of a flexible resilient material, e.g., a plastic, so that the shoulder of the top member can be forced past the lip of the bottom member when the circumferential wall of the top member is inserted into the bottom member. The ceiling has a shoulder engageable with the edge of the bottom member circumferential wall for limiting relative inward movement between the top member and the bottom member.

There is a groove between the ceiling shoulder and the edge of the bottom member circumferential wall at least when the top and bottom members are not at minimum separation.

The floor of the bottom member and the ceiling of the top member are substantially parallel, and the reservoir, when full expanded, has a dimension parallel to the axis substantially equal to the distance between the ceiling and the floor at maximum separation. The ceiling is generally symmetric in shape to the floor.

The invention also provides for mounting the housing of the scent sampler in a planar sign having an opening with an inner edge congruent to a profile of the circumferential wall of the top member, and sized to enable the sampler to be pressed into the sign opening with an edge of the sign opening captured within the groove whereby the top member and the bottom member can be squeezed together for compressing the reservoir to force the mixture into the adjacent ambient air.

One of the outer wall of the ceiling and the floor can have a raised boss on its outer surface through which the aperture passes. The raised boss can be received within an opening, in a label, congruent to a circumference of the raised boss for alignment of the label on the one of the ceiling and the floor.

DESCRIPTION OF THE DRAWINGS

Referring now to the drawings.

DESCRIPTION OF THE PREFERRED EMBODIMENT

Figure 1:
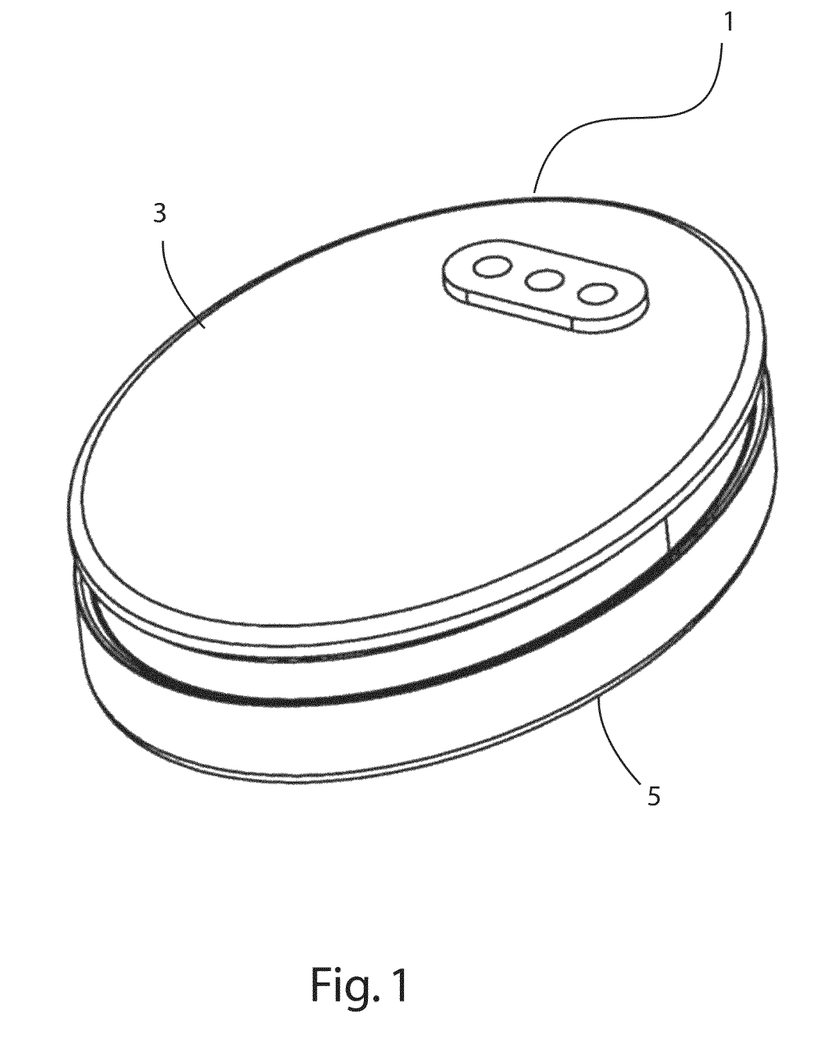
FIG. 1 is a perspective view of a preferred embodiment of the invention.
Figure 2:
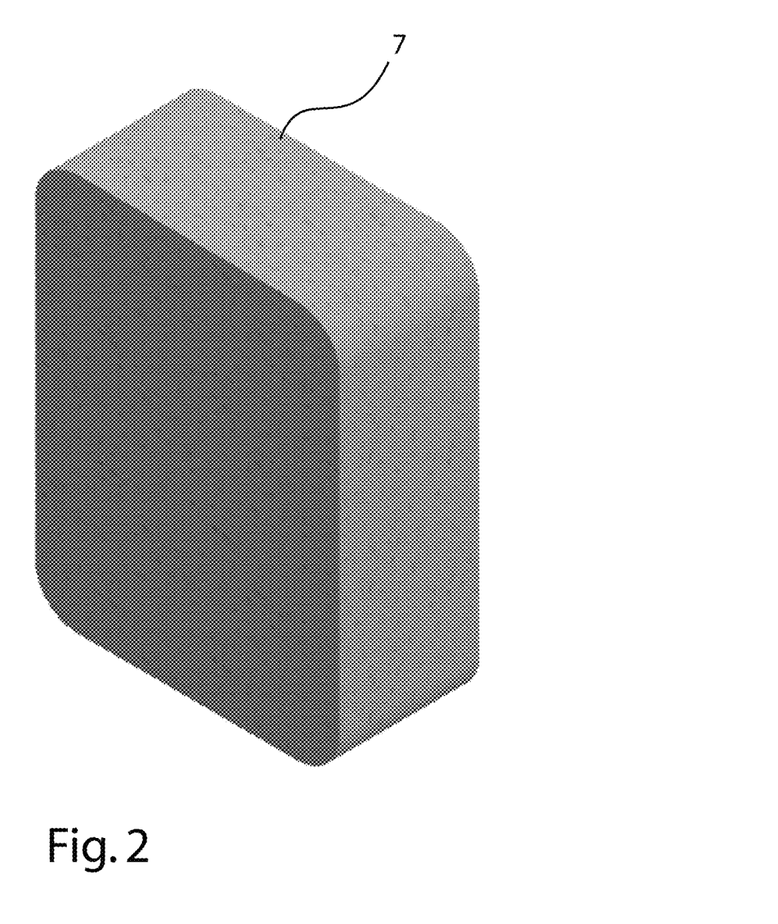
FIG. 2 is a perspective view of a component of the preferred embodiment of the invention.
Figure 3:
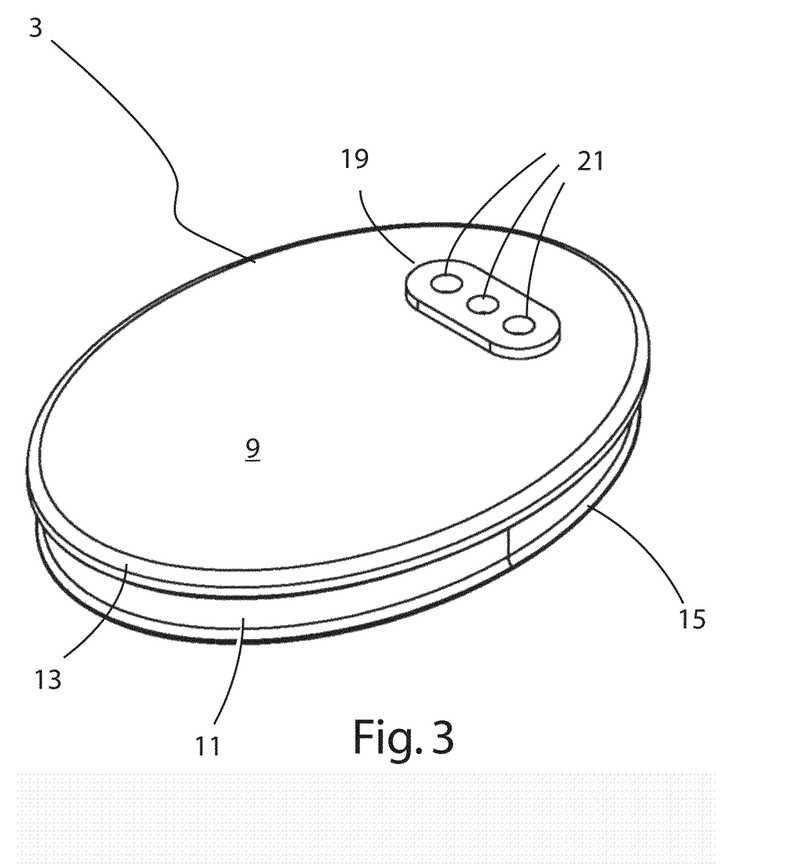
FIG. 3 is a perspective view of another component of the preferred embodiment of the invention.
Figure 4:
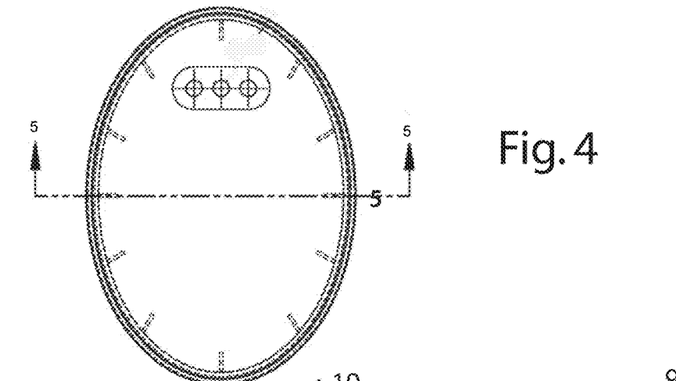
FIG. 4 is a top plan view of the component of the preferred embodiment of the invention shown in FIG. 3.
Figure 5:
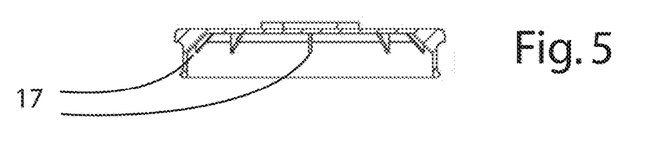
FIG. 5 is a sectional elevation view taken through line 5-5 of FIG. 4.
Figure 6:
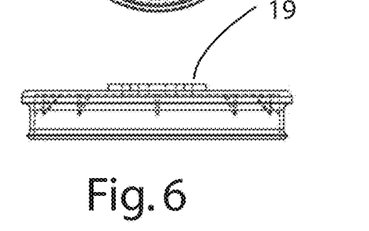
FIG. 6 is an end elevation view of the component of the preferred embodiment of the invention shown in FIG. 3.
Figure 7:
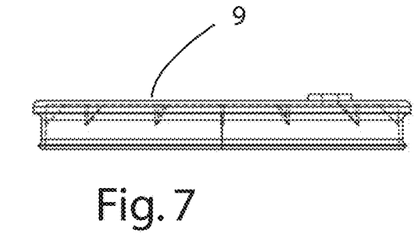
FIG. 7 is a side elevation view of the component of the preferred embodiment of the invention shown in FIG. 3.
Figure 8:
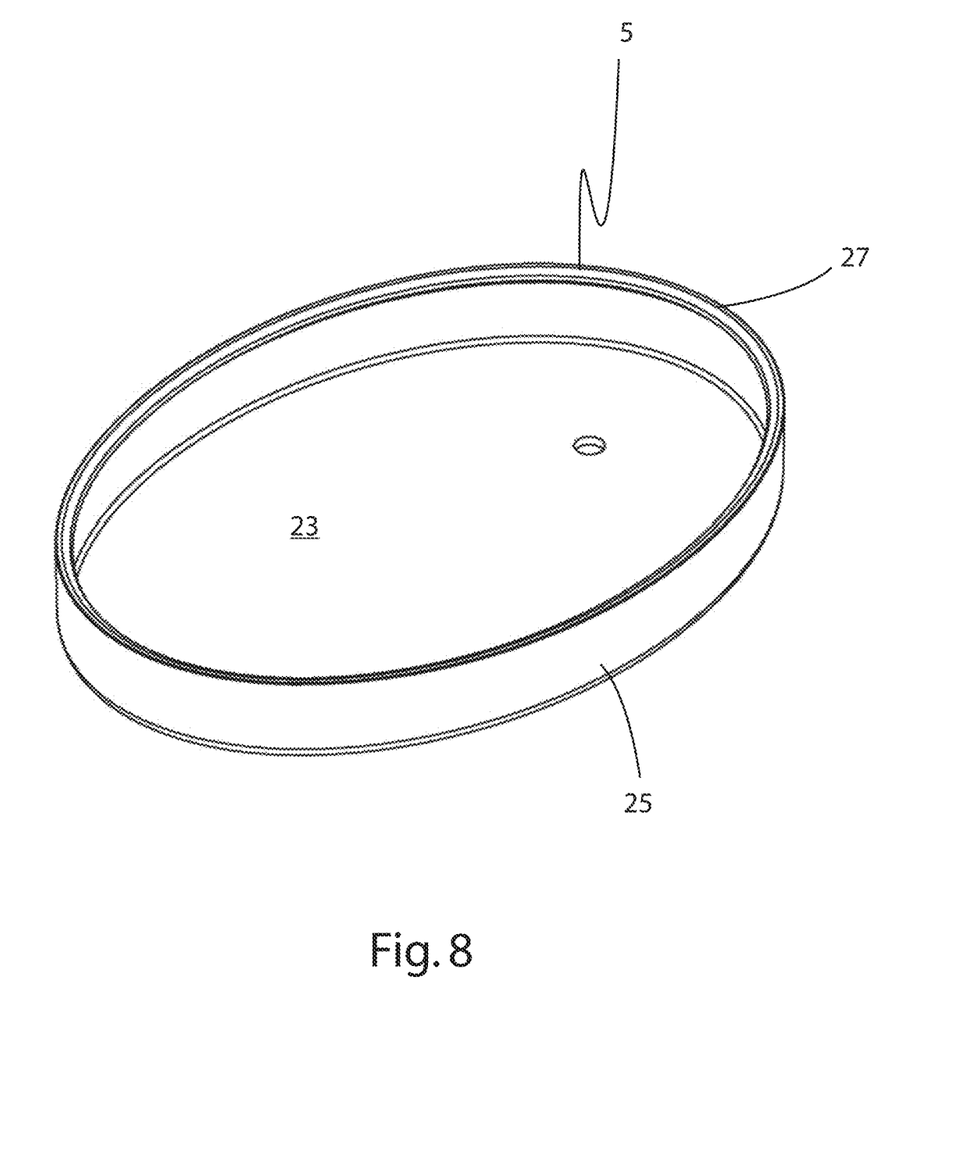
FIG. 8 is a perspective view of still another member of the preferred embodiment of the invention.
Figure 9:
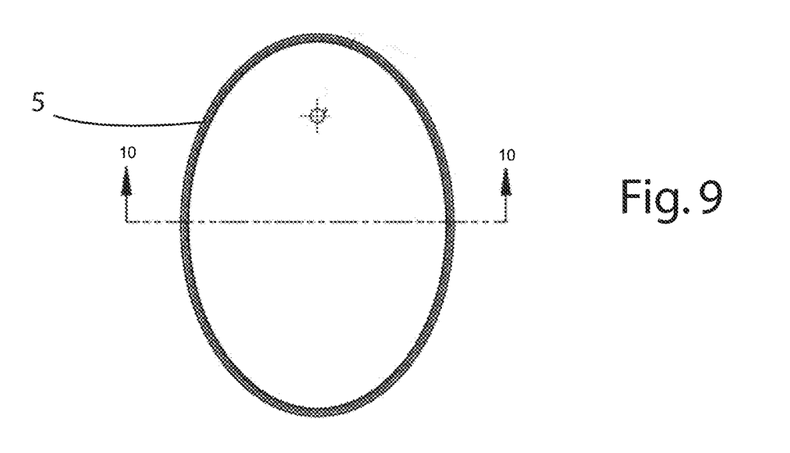
FIG. 9 is a top plan view of the component of the preferred embodiment of the invention shown in FIG. 8.
Figure 10:
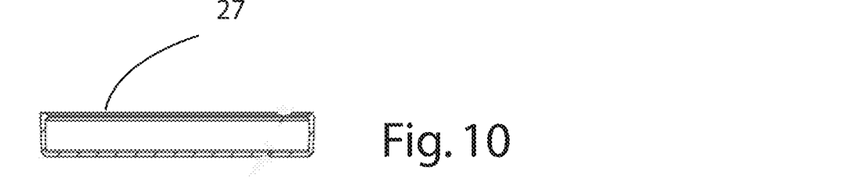
FIG. 10 is a sectional elevation view taken through line 10-10 of FIG. 9.
Figure 11:
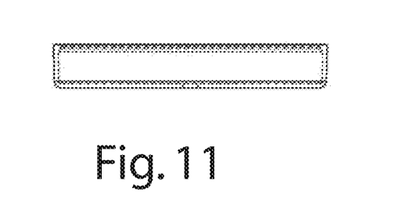
FIG. 11 is an end elevation view of the component of the preferred embodiment of the invention shown in FIG. 8.
Figure 12:
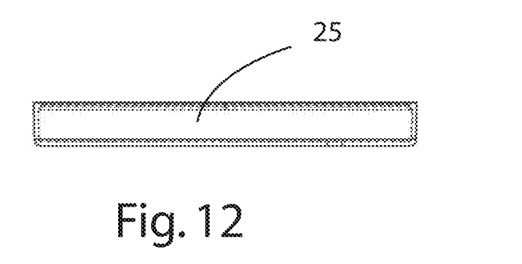
FIG. 12 is a side elevation view of the component of the preferred embodiment of the invention shown in FIG. 8.
Figure 13:
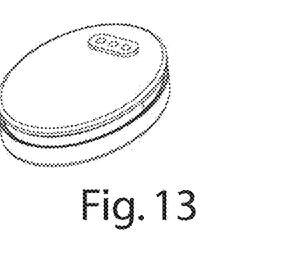
FIG. 13 is a perspective view of the preferred embodiment of the invention shown in a first disposition.
Figure 14:
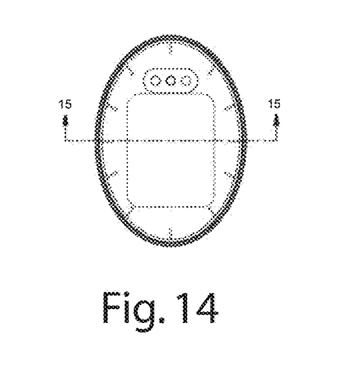
FIG. 14 is a top plan view of the preferred embodiment of the invention in the disposition shown in FIG. 13.
Figure 15:
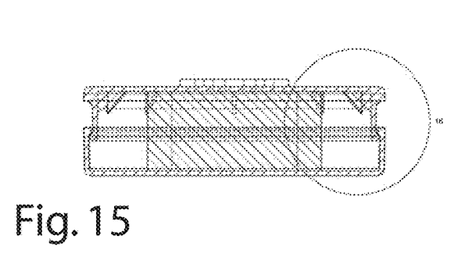
FIG. 15 is a sectional elevation view of the preferred embodiment of the invention in the disposition shown in FIG. 13, taken through line 15-15 of FIG. 14.
Figure 16:
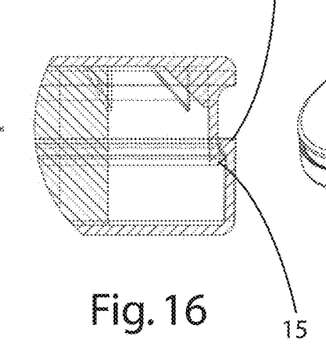
FIG. 16 is an enlarged fragmentary sectional elevation view of the preferred embodiment of the invention as shown in FIG. 15.

Referring now to FIG. 1 of the drawings there is shown a scent sampler 1 for spraying a mixture of air and a vapor released from a fragrance oil by evaporation. The sampler 1 is assembled from three members, namely a top member 3 in the form of an open elliptical bin, a bottom member 5 also in the form of an open elliptical bin, and a reservoir 7 in the form of a pillow-shaped block made of a spongy resilient absorbent hydrophilic material, e.g., foam, shown in FIG. 2, into which the fragrance oil from which the scent is to be sprayed is injected and absorbed. The foam from which the reservoir 7 is made is preferably an open cell polyester hydrophilic foam. This foam has been found to have excellent retention properties with respect to fragrance oils and can be expected to have a useful life, without replenishment, substantially greater than felt and other porous materials used in prior art fragrance dispensing devices.

Referring now to FIGS. 3-7, the top member 3 has a planar ceiling 9 of oval or elliptical shape. Extending orthogonally downward from the ceiling 9 is a continuous circumferential wall 11 of uniform height slightly inset from the outermost edge thereby leaving an outwardly extending lip 13 forming a top edge of the top member 3. Another outwardly directed lip 15 runs about the edge of the wall 11 distal from the ceiling 9. Spaced integral braces 17 between the ceiling 9 and wall 11 are molded into the top member 3 for enhancing the structural integrity of the top member 3.

A rectangular boss 19 with rounded ends is formed on the outside surface of the ceiling 9 adjacent one of its ends. Three aligned equally spaced apertures 21 pass through the boss 19 and underlying ceiling 9.

Referring to FIG. 8-12 of the drawings, the bottom member 5 is generally symmetric in shape to the top member 3. The bottom member 5 has a planar floor 23 of oval or elliptical shape. Extending orthogonally upward from the floor 23 is a continuous circumferential wall 25 of uniform height substantially equal to the height of the wall 11 of the top member 3. The bottom member wall 25 has, at its edge distal from the floor 23, an inwardly directed lip 27.

The outer surface of the wall 11 of the top member 3 has a circumference slightly less than the inner circumference of the wall 25 of the bottom member 5. The outer circumference of the lip 15 on the top member 3 is slightly greater than the inner circumference of the lip 27 on the bottom member 5.

The top member 3 and bottom member 5 are molded from a resilient material, e.g., plastic, so that the lip 15 of the top member 3 can be forced past the lip 27 on the bottom member 5 as the wall 11 of the top member 3 is inserted into the bottom member 5. This arrangement permits telescoping of the top member 3 within the bottom member 5 between an expanded disposition whereat the top of the lip 15 of the top member 3 engages the bottom of the lip 27 of the bottom member 5 for preventing separation of the top member 3 from the bottom member 5.

It has been found that injection molded polypropylene provides the necessary properties of rigidity, reduced friction between the outer surface of the lip 15 of the top member and the inner surface of the wall 25 of the bottom member during telescoping of the top member 3 within the bottom member 5, and sufficient flexibility to enable the top member 3 to be forced into the bottom member 5.

Figure 17A:
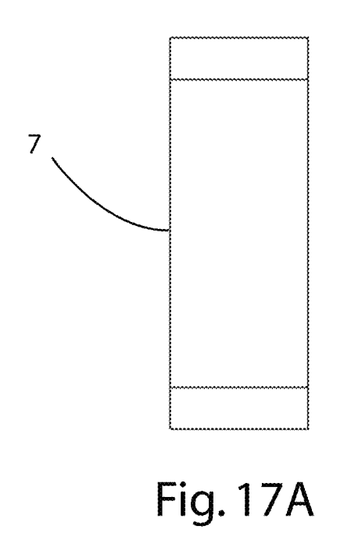
FIG. 17A is a side elevation view of the component of the preferred embodiment of the invention shown in FIG. 2 in the disposition shown in FIGS. 13-16.

The dual function reservoir 7 of foam or other spongy material having the properties of absorbance and resiliency is placed within the chamber formed by the space to be enclosed by the top member 3 and bottom member 5. The reservoir 7 is preferably in the shape of a rectangular parallelepiped and has a dimension in a direction orthogonal to the floor 23 and ceiling 9 of the bottom member 5 and top member 3 substantially equal to the maximum distance between the inner surfaces of the ceiling 9 of the top member 3 and floor 23 of the bottom member 5 when the top member 3 and bottom member 5 are at positions of maximum separation, i.e., where the sampler 1 is in its maximum expanded disposition as shown in FIGS. 13-16 whereat the lip 15 and shoulder 27 are in engagement. In this disposition, the reservoir 7 is in a relaxed condition as shown in FIG. 17A.

Figure 17B:
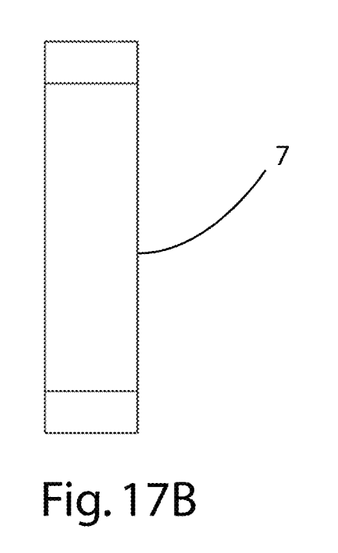
FIG. 17B is a side elevation view of the component of the preferred embodiment of the invention shown in FIG. 2 in a second disposition.
Figure 18:
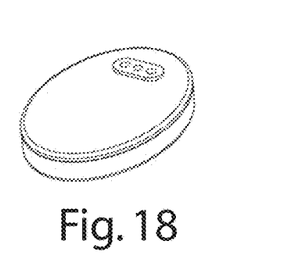
FIG. 18 is a perspective view of the preferred embodiment of the invention with the component of FIG. 17B in the second disposition.
Figure 19:
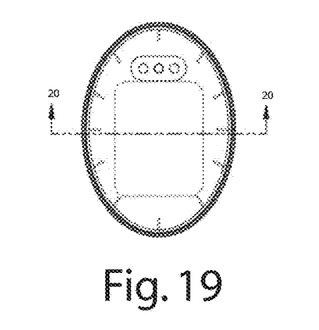
FIG. 19 is a top plan view of the preferred embodiment of the invention in the disposition shown in FIG. 18.
Figure 20:
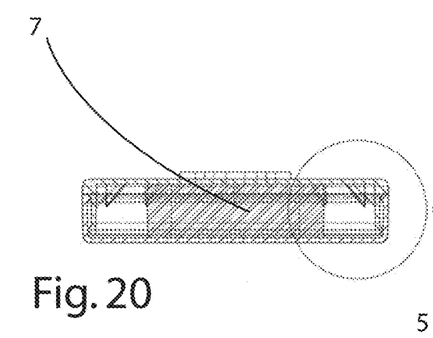
FIG. 20 is a sectional elevation view of the preferred embodiment of the invention in the disposition shown in FIG. 19, taken through line 20-20.
Figure 21:
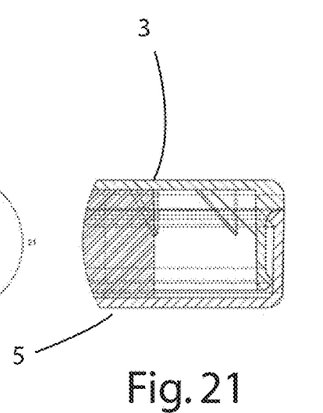
FIG. 21 is an enlarged fragmentary sectional elevation view of the preferred embodiment of the invention as shown in FIG. 20.

When the top and bottom members 3, 5 are urged together toward a position of minimum separation of the floor 23 of the bottom member 5 and ceiling 9 of the top member 3 as shown in FIGS. 18-21, the reservoir 7 is compressed as seen in FIG. 17B. Compression of the reservoir 7 is resisted by its resiliency so that upon release of the squeezing force exerted to move the top member 3 and bottom member 5 toward one another, the reservoir 7 acts as a compressed spring and urges the top member 3 and bottom member 5 apart toward their at rest positions of maximum separation.

A mixture of the air within the sampler 1 and fragrance evaporated from the fragrance oil absorbed into the reservoir 7 is forced through the apertures 21 to the ambient environment when the volume of the fragrance air mixture within the sampler 1 is reduced by squeezing the top member 3 and bottom member 5 toward one another. As the squeezing force is reduced or removed, and the resilient reservoir 7 urges the top member 3 and bottom member 5 apart, air is drawn from the ambient environment through the apertures 21 into the interior of the sampler 1.

Figure 22:
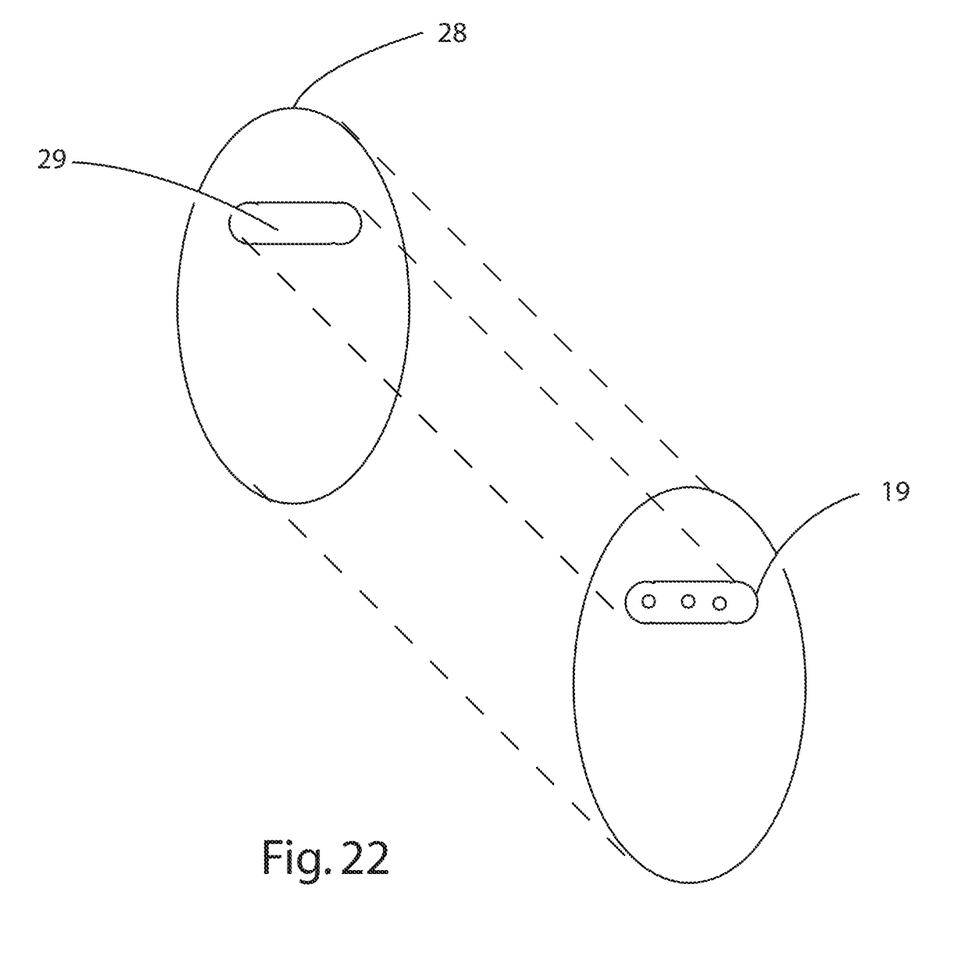
FIG. 22 is an exploded schematic view of the preferred embodiment of the invention with an optional component.

The raised boss 19 serves as a template for positioning a label 28 to be applied to the outer surface of the top member 3 of the sampler 1 as can be seen in FIG. 22. The label 28 has a die cut opening 29 congruent to the profile of the boss 19. When the opening 29 in the label 28 is fitted over the boss 19, label 29 aligns with the outer surface of the top member 3. The underside of the label 28 is provided with a pressure sensitive adhesive for adhesion to the top member 3.

Figures 23, 24:
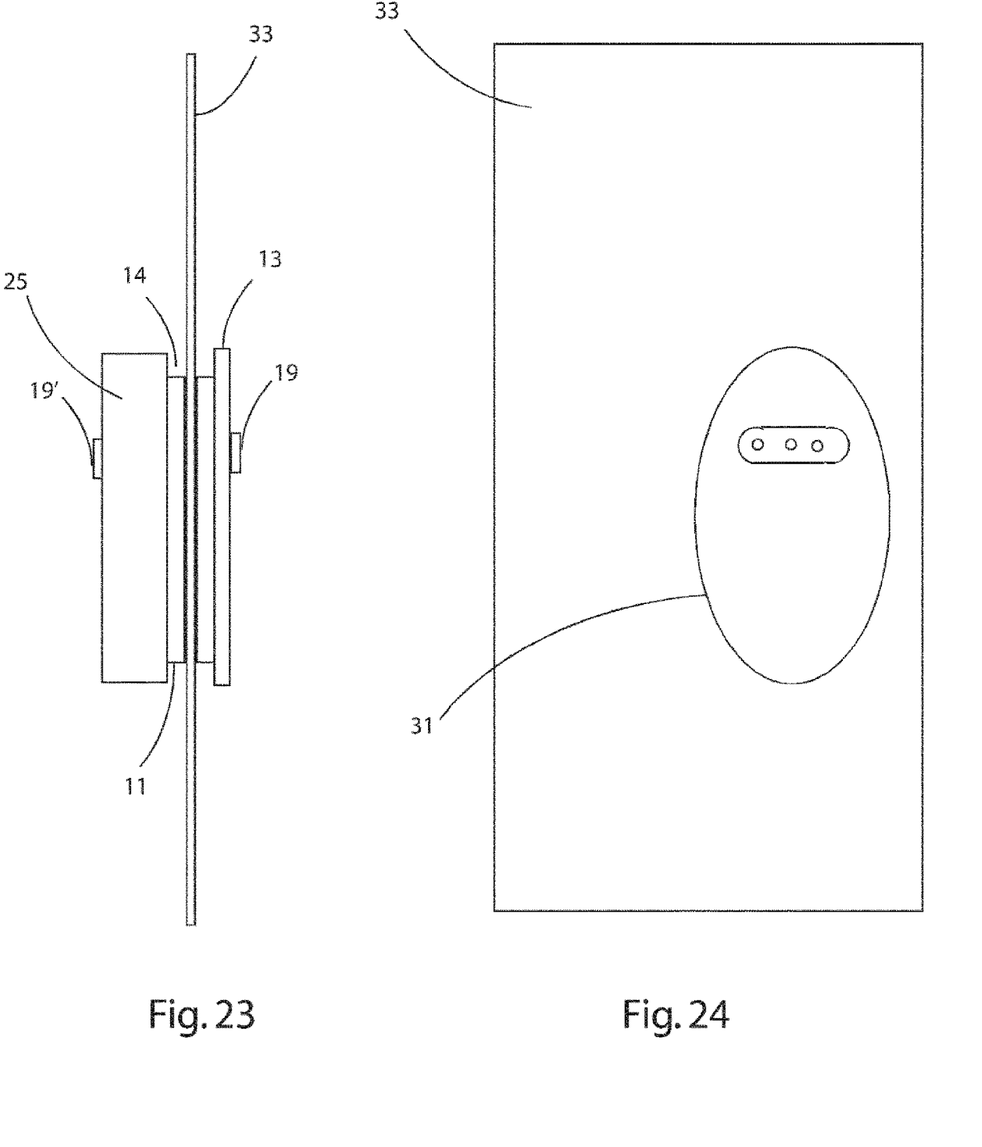
FIG. 23 is a side elevation view of the preferred embodiment of the invention in an optional environment.
FIG. 24 is a front elevation view of the preferred embodiment of the invention in the environment shown in FIG. 23.

Referring now to FIGS. 23 and 24, when the sampler 1 is assembled and is in its at rest disposition with the resilient reservoir 7 expanded, the exposed outer surface of the wall 11 of the top member 3 defines a groove between the lip 13 of the top member 3 and the edge of wall 25 of the bottom member 5 distal from the floor 23.

An oval or elliptical opening 31 in a cardboard display sign 33, having an inner edge congruent to the top profile of the outer edge of the wall 11 of the top member 3 enables the sampler 1 to be pressed into and captured within the sign opening 31 and mounted therein with the edge of the cardboard surrounding the opening 31 in light frictional engagement with the wall 11 of the top member 3. The height of the wall 11 of the top member 3 is sufficiently greater than the thickness of the cardboard to permit the sampler 1 to be squeezed and the reservoir 7 to be partially compressed enough to force an air-fragrance mixture into the adjacent atmosphere without removing the sampler 1 from the cardboard display sign 33. In order to permit sampling of the scent from either side of the cardboard display, the outer surface of the floor 23 can be provided with a boss 19', identical to the boss 19, with apertures that penetrate the member 5 so that fragranced air can escape from either side of the sampler 1 when squeezed and each member of the sampler can receive a label. Appropriate graphics on the display sign 33 can attract a consumer and provide instructions for sampling a fragrance without removing the sampler 1 from the display sign 33.

In addition to use of the invention for sampling fragrances, it may be left as an unattended air freshener in a place desired to be freshened by the aroma of the scent, e.g., in a closet, a furniture drawer or an item of luggage. Depending on the nature and concentration of the scent, the invention can also serve as a visually pleasing room deodorizer.

It is to be appreciated that the foregoing specification describes a preferred embodiment of the invention to which modifications may be made without departing from the spirit and scope of the invention. For example, although the sampler 1 of the preferred embodiment is oval or elliptical in shape, it may be made of virtually any shape, e.g., circular, square, or rectangular, provided that the top member can be slidingly captured for telescoping with respect to the bottom member.

What is claimed is:

1. A scent sampler comprising
a compressible and expandable housing having top and bottom members, one inverted relative to and telescopically mounted within the other for relative reciprocation along an axis, between maximum and minimum separation of said top and bottom members, each of said top and bottom members comprising a major wall substantially transverse to said axis and a circumferential wall extending orthogonally inwardly from said major wall in a direction parallel to said axis,
said major wall of said top member being a ceiling of said housing and said major wall of said bottom member being a floor of said housing,
said housing having a chamber of variable volume enclosed by said ceiling, said floor, said circumferential wall of said top member and said circumferential wall of said bottom member, said housing having an aperture through which air can travel between said chamber and the ambient environment, an outer surface of said circumferential wall of said top member being in frictional sliding engagement with an inner surface of said circumferential wall of said bottom member, and a resilient, compressible, absorbent, elastic reservoir within said chamber for absorbing a scented liquid, said reservoir having a dimension greater than said minimum separation so that during squeezing of said top and bottom members toward one another, said reservoir is compressed and releases into said chamber a vapor of said scented liquid which forms a mixture with the air in said chamber, at least a portion of said mixture being released into the ambient environment through said aperture, and upon cessation of said squeezing said reservoir urges said top and bottom members apart toward maximum separation as said reservoir returns to an uncompressed state drawing ambient air from the ambient environment into said chamber, wherein said bottom member has, along an edge of its circumferential wall distal from its floor, a shoulder extending inwardly in a direction generally parallel to said floor, and said top member has, along an edge of its circumferential wall distal from said ceiling, a lip extending outwardly in a direction generally parallel to said ceiling in interfering relationship to said shoulder for capturing said top member within said bottom member and preventing complete separation of said top member and said bottom member.

2. A scent sampler according to claim 1 wherein at least one of said top member and said bottom member is made of a flexible resilient material so that said shoulder of said top member can be forced past said lip of said bottom member when said circumferential wall of said top member is inserted into said bottom member.

3. A scent sampler according to claim 1 wherein said ceiling has a shoulder engageable with said edge of said bottom member circumferential wall for limiting relative inward movement between said top member and said bottom member.

4. A scent sampler according to claim 1 wherein said reservoir comprises a hydrophilic material.

5. A scent sampler according to claim 1 wherein said reservoir comprises a spongy material.

6. A scent sampler according to claim 1 wherein said floor of said bottom member and said ceiling of said top member are substantially parallel, and said reservoir, when fully expanded, has a dimension parallel to said axis substantially equal to the distance between said ceiling and said floor at maximum separation.

7. A scent sampler according to claim 1 wherein said ceiling is generally symmetric in shape to said floor.

8. A scent sampler according to claim 1 wherein one of said ceiling and said floor has a raised boss on its outer surface through which said aperture passes.

9. A scent sampler according to claim 8 further comprising a label with an opening congruent to a circumference of said raised boss, said raised boss being receivable within said label opening for alignment of said label on said one of said ceiling and said floor.

10. A display comprising a scent sampler according to claim 1 and a planar sign having an opening with an inner edge congruent to a profile of said circumferential wall of said top member, and sized to enable said sampler to be pressed into said sign opening with an edge of said sign opening captured within a groove between said top member and said bottom member whereby said top member and said bottom member can be squeezed together for compressing said reservoir.

* * * * *